(12) United States Patent
Ross

(10) Patent No.: US 6,444,799 B1
(45) Date of Patent: Sep. 3, 2002

(54) P. GINGIVALIS POLYNUCLEOTIDES AND USES THEREOF

(75) Inventor: Bruce Carter Ross, Victoria (AU)

(73) Assignee: CSL Limited, Parkville (AU)

( * ) Notice: Subject to any disclaimer, the term of this patent is extended or adjusted under 35 U.S.C. 154(b) by 0 days.

(21) Appl. No.: 09/221,017

(22) Filed: Dec. 23, 1998

(30) Foreign Application Priority Data

| Dec. 31, 1997 | (AU) | PP1182 |
| Jan. 30, 1998 | (AU) | PP1546 |
| Apr. 9, 1998 | (AU) | PP2911 |
| May 22, 1998 | (AU) | PP3654 |
| Dec. 10, 1998 | (WO) | PCT/AU98/01023 |

(51) Int. Cl.$^7$ ............ C07H 21/02; C12Q 1/68
(52) U.S. Cl. ........ 536/23.1; 536/23.7; 536/24.1; 536/24.32; 435/6; 435/69.1; 435/320.1; 435/471; 435/476; 514/44
(58) Field of Search ........ 435/6, 69.1, 320.1, 435/471, 476; 536/23.1, 24.1, 23.7, 24.32; 514/44

(56) References Cited

PUBLICATIONS

AE000833, GENBANK, Nov. 15, 1997.*
B31729, GENBANK, Oct. 17, 1997.*
N97733, GENBANK, Nov. 18, 1996.*
AC004564, GENBANK, Nov. 2, 1998.*

Borodovsky, M. et al. (1994). "Intrinsic and Extrinsic Approaches for Detecting Genes in a Bacterial Genome," *Nucl. Acids Res.* 22, 4756–4767.

Donnelly et al. (1995). "Immunization with DNA," *J. Immunol. Meth.* 176, 145–152.

Fleischmann et al. (1995). "Whole–genome Random Sequencing and Assembly of Haemophilus inluenza," *Science* 269, 496–512.

Marmur, J. (1961). "A Procedure for the Isolation of Deoxyribonucleic Acid from Microorganisms," *J. Mol. Biol.* 3, 208–218.

* cited by examiner

*Primary Examiner*—Mary K. Zeman
(74) *Attorney, Agent, or Firm*—Morrison & Foerster LLP

(57) ABSTRACT

The present invention relates to isolated *Porphorymonas gingivalis* polynucleotides. The polynucleotides comprises a contiguous sequence of at least 20 nucleotides which is identical to a contiguous sequence of at least 20 nucleotides within a sequence selected from the group consisting of SEQ. ID. NO. 1 to SEQ. ID. NO. 1120 and sequences complementary thereto.

17 Claims, No Drawings

P. GINGIVALIS POLYNUCLEOTIDES AND USES THEREOF

FIELD OF THE INVENTION

The present invention relates to P. gingivalis polynucleotides and to the use of these polynucleotides in the production of nucleotide probes for detection of P. gingivalis. The polynucleotides may also be used in the production of recombinant P. gingivalis polypeptides. The polynucleotides and recombinant polypeptides can also be used in compositions for use in raising an immune response in a subject against P. gingivalis and treating or preventing or reducing the severity of the condition known as periodontitis.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is P. gingivalis as the recovery of this microorganism from adult periodontitis lesions can be up to 50% of the subgingival anaerobically cultivable flora, whereas P. gingivalis is rarely recovered, and then in low numbers, from healthy sites. A proportional increase in the level of P. gingivalis in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of P. gingivalis. These findings in both animals and humans suggest a major role for P. gingivalis in the development of adult periodontitis.

P. gingivalis is a black-pigmented, anaerobic, asaccharolytic, proteolytic Gram-negative rod that obtains energy from the metabolism of specific amino acids. The microorganism has an absolute growth requirement for iron, preferentially in the form of haeme or its Fe(III) oxidation product haemin and when grown under conditions of excess haemin is highly virulent in experimental animals. A number of virulence factors have been implicated in the pathogenicity of P. gingivalis including the capsule, adhesins, cytotoxins and extracellular hydrolytic enzymes.

SUMMARY OF THE INVENTION

The present inventors have isolated P. gingivalis polynucleotides sequences which can be used to develop nucleotide probes specific for P. gingivalis. These probes are of particular use in the detection of P. gingivalis infection. Further the polynucleotides can be used for recombinant production of P. gingivalis polypeptides.

Accordingly, in a first aspect the present invention consists in an isolated polynucleotide of at least 20 nucleotides, the polynucleotide comprising a contiguous sequence of at least 20 nucleotides which is identical to a contiguous sequence of at least 20 nucleotides within a sequence selected from the group consisting of SEQ. ID. NO. 1 to SEQ. ID. NO. 1120 and sequences complementary thereto.

In a preferred embodiment of the present invention the polynucleotide is at least 30 nucleotides, preferably at least 50 nucleotides and more preferably at least 100 nucleotides.

In a further preferred embodiment the polynucleotide comprises a contiguous sequence of at least 30 nucleotides which is identical to a contiguous sequence of at least 30 nucleotides within a sequence selected from the group consisting of SEQ. ID. NO. 1 to SEQ. ID. NO. 1120 and sequences complementary thereto, preferably the polynucleotide comprises a contiguous sequence of at least 50 nucleotides which is identical to a contiguous sequence of at least 50 nucleotides within a sequence selected from the group consisting of SEQ. ID. NO. 1 to SEQ. ID. NO. 1120 and sequences complementary thereto, and more preferably the polynucleotide comprises a contiguous sequence of at least 100 nucleotides which is identical to a contiguous sequence of at least 100 nucleotides within a sequence selected from the group consisting of SEQ. ID. NO. 1 to SEQ. ID. NO. 1120 and sequences complementary thereto.

In a second aspect the present invention consists in an isolated polynucleotide, the polynucleotide comprising at least 20 nucleotides, the polynucleotide having a sequence which hybridises under stringent conditions to a sequence selected from the group consisting of SEQ. ID. NO. 1 to SEQ. ID. NO. 1120 and sequences complementary thereto.

It is preferred that the polynucleotide is at least 30 nucleotides, preferably at least 50 nucleotides, and more preferably at least 100 nucleotides.

It is also preferred that the polynucleotide is DNA.

In a preferred embodiment of the present invention the polynucleotide further comprises a detectable label. Non-limiting examples of labels which may be used include biotin, radio isotopes, fluorescent labels etc.

The present invention also provides method for detecting the presence of P. gingivalis nucleic acid in a sample comprising:

(a) contacting a sample with the polynucleotide of the present invention under conditions in which a hybrid can form between the polynucleotide and a P. gingivalis nucleic acid in the sample; and (b) detecting the hybrid formed in step (a), wherein detection of a hybrid indicates the presence of a P. gingivalis nucleic acid in the sample.

As will be readily appreciated by those skilled in the art the polynucleotides of the present invention can be used to produce P. gingivalis polypeptides. This may achieved using any of a number of methods well known in the art, however, this will typically involve the use of a recombinant expression vector comprising the DNA of the present invention operably linked to a transcription regulatory element. It is preferred that the DNA is operably linked to a transcription regulatory element. This recombinant expression can be used in the transformation of an appropriate cell.

The transformed cell can then be used to produce P. gingivalis polypeptides. This involves culturing the cell under conditions that permit expression of the polypeptide and recovering the polypeptide.

The nucleotides of the present invention can also be used to raise an immune response in an animal by DNA vaccination. Accordingly the present invention also provides a composition for use in raising an immune response directed against P. gingivalis in a subject, the composition comprising an effective amount of at least one DNA molecule of the present invention and a pharmaceutically acceptable carrier. It is preferred that the pharmaceutically acceptable carrier is an adjuvant.

DETAILED DESCRIPTION

Definitions

A purified or isolated polypeptide or a substantially pure preparation of a polypeptide are used interchangeably herein and, as used herein, mean a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 mg of the polypeptide.

A purified preparation of cells refers to, in the case of plant or animal cells, an in vitro preparation of cells and not an entire intact plant or animal. In the case of cultured cells or microbial cells, it consists of a preparation of at least 10% and more preferably 50% of the subject cells.

A purified or isolated or a substantially pure nucleic acid, e.g., a substantially pure DNA, (are terms used interchangeably herein) is a nucleic acid which is one or both of the following: not immediately contiguous with both of the coding sequences with which it is immediately contiguous (i.e., one at the 5' end and one at the 3' end) in the naturally occurring genome of the organism from which the nucleic acid is derived; or which is substantially free of a nucleic acid with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional *P. gingivalis* DNA sequence.

A "contig" as used herein is a nucleic acid representing a continuous stretch of genomic sequence of an organism.

An "open reading frame", also referred to herein as ORF, is a region of nucleic acid which encodes a polypeptide. This region may represent a portion of a coding sequence or a total sequence and can be determined from a stop to stop codon or from a start to stop codon.

As used herein, a "coding sequence" is a nucleic acid which is transcribed into messenger RNA and/or translated into a polypeptide when placed under the control of appropriate regulatory sequences. The boundaries of the coding sequence are determined by a translation start codon at the five prime terminus and a translation stop code at the three prime terminus. A coding sequence can include but is not limited to messenger RNA synthetic DNA, and recombinant nucleic acid sequences.

A "complement" of a nucleic acid as used herein refers to an anti-parallel or antisense sequence that participates in Watson-Crick base-pairing with the original sequence.

A "gene product" is a protein or structural RNA which is specifically encoded by a gene.

As used herein, the term "probe" refers to a nucleic acid, peptide or other chemical entity which specifically binds to a molecule of interest. Probes are often associated with or capable of associating with a label. A label is a chemical moiety capable of detection. Typical labels comprise dyes, radioisotopes, luminescent and chemiluminescent moieties, fluorophores, enzymes, precipitating agents, amplification sequences, and the like. Similarly, a nucleic acid, peptide or other chemical entity which specifically binds to a molecule of interest and immobilizes such molecule is referred herein as a "capture ligand". Capture ligands are typically associated with or capable of associating with a support such as nitro-cellulose, glass, nylon membranes, beads, particles and the like. The specificity of hybridization is dependent on conditions such as the base pair composition of the nucleotides, and the temperature and salt concentration of the reaction. These conditions are readily discernible to one of ordinary skill in the art using routine experimentation.

Homologous refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared $\times 100$.

The terms peptides, proteins, and polypeptides are used interchangeably herein.

An "immunogenic component" as used herein is a moiety, such as an *P. gingivalis* polypeptide, analog or fragment thereof, that is capable of eliciting a humoral and/or cellular immune response in a host animal. An "antigenic component" as used herein is a moiety, such as *P. gingivalis* polypeptide, analog or fragment thereof, that is capable of binding to a specific antibody with sufficiently high affinity to form a detectable antigen-antibody complex.

As used herein, the term "cell-specific promoter" means a DNA sequence that serves as a promoter, i.e., regulates expression of a selected DNA sequence operably linked to the promoter, and which effects expression of the selected DNA sequence in specific cells of a tissue. The term also covers so-called "leaky" promoters, which regulate expression of a selected DNA primarily in one tissue, but cause expression in other tissues as well.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include at a minimum, all components whose presence is necessary for expression, and may also include additional components whose presence is advantageous, for example, leader sequences.

As used herein, the term "operably linked" refers to sequences joined or ligated to function in their intended manner. For example, a control sequence is operably linked to coding sequence by ligation in such a way that expression of the coding sequence is achieved under conditions compatible with the control sequence and host cell.

A "sample" as used herein refers to a biological sample, such as, for example, tissue or fluid isolated from an individual (including without limitation plasma, serum, cerebrospinal fluid, lymph, tears, saliva and tissue sections) or from in vitro cell culture constituents, as well as samples from the environment.

The practice of the invention will employ, unless otherwise indicated, conventional techniques of chemistry, molecular biology, microbiology, recombinant DNA, and immunology well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1–4, IRL Press (1995 and 1996), and F. M. Ausubel et al. (Editors), Current Protocols in Molecular Biology, Greene Pub. Associates and Wiley-Interscience (1988, including all updates until present). The disclosure of these texts are incorporated herein by reference.

Pharmaceutically Acceptable Carriers

The antibodies, polypeptides and DNA of the present invention can be included in compositions which include a carrier or diluent. These compositions include pharmaceutical compositions where the carrier or diluent will be pharmaceutically acceptable. Pharmaceutically acceptable carriers or diluents include those used in compositions suitable for oral, rectal, nasal, topical (including buccal and sublingual), vaginal, parenteral (including subcutaneous, intramuscular, intravenous, intradermal, intrathecal and epidural) administration. They are non-toxic to recipients at the dosages and concentrations employed. Representative examples of pharmaceutically acceptable carriers or diluents include, but are not limited to; water, isotonic solutions which are preferably buffered at a physiological pH (such as phosphate-buffered saline or Tris-buffered saline) and can also contain one or more of, mannitol, lactose, trehalose, dextrose, glycerol, ethanol or polypeptides (such as human serum albumin). The compositions may conveniently be presented in unit dosage form and may be prepared by any of the methods well known in the art of pharmacy.

Mutants, Variants and Homology—Nucleic Acids

Mutant polynucleotides will possess one or more mutations which are deletions, insertions, or substitutions of nucleotide residues. Mutants can be either naturally occurring (that is to say, isolated from a natural source) or synthetic (for example, by performing site-directed metagenesis on the DNA). It is thus apparent that polynucleotides of the invention can be either naturally occurring or recombinant (that is to say prepared using recombinant DNA techniques).

An allelic variant will be a variant that is naturally occurring within an individual organism.

Nucleotide sequences are homologous if they are related by divergence from a common ancestor. Consequently, a species homologue of the polynucleotide will be the equivalent polynucleotide which occurs naturally in another species. Within any one species a homologue may exist as numerous allelic variants, and these will be considered homologues of the polynucleotide. Allelic variants and species homologues can be obtained by following standard techniques known to those skilled in the art.

Adjuvants

"Adjuvant" means a composition comprised of one or more substances that enhances the immunogenicity and efficacy of a vaccine composition. Non-limiting examples of suitable adjuvants include squalane and squalene (or other oils of animal origin); block copolymers; detergents such as Tween®-80; Quil® A, mineral oils such as Drakeol or Marcol, vegetable oils such as peanut oil; Corynebacterium-derived adjuvants such as *Corynebacterium parvum*; Propionibacterium-derived adjuvants such as *Propionibacterium acne; Mycobacterium bovis* (Bacillus Calmetic and Guerinn or BCG); interleukins such as interleukin 2 and interleukin-12; monokines such as interleukin 1; tumour necrosis factor; interferons such as gamma interferon; combinations such as saponin-aluminium hydroxide or Quil-A aluminium hydroxide; liposomes; ISCOM adjuvant; mycobacterial cell wall extract; synthetic glycopeptides such as muramyl dipeptides or other derivatives; Avridine; Lipid A; dextran sulfate; DEAE-Dextran or DHAE-Dextran with aluminium phosphate; carboxypolymethylene such as Carbopol' EMA; acrylic copolymer emulsions such as Neocryl A640 (e.g. U.S. Pat. No. 5,047,238); vaccinia or animal posvirus proteins; sub-viral particle adjuvants such as cholera toxin, or mixtures thereof.

As used herein, stringent conditions are those that (1) employ low ionic strength and high temperature for washing, for example, 0.015 M NaCl/0.0015 M sodium citrate/0.1% NaDodSO4 at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS and 10% dextran sulfate at 42° C. in 0.2×SSC and 0.1% SDS As will be understood the present invention includes within its scope DNA vaccination. Further information regarding DNA vaccination may be found in Donnelly et al, Journal of Immunological Methods 176(1994) 145–152, the disclosure of which is incorporated herein by reference. Throughout this specification the word "comprise", or variations such as "comprises" or "comprising", will be understood to imply the inclusion of a stated element or integer or group of elements or integers but not the exclusion of any other element or integer, or group of elements or integers.

Preparation of the *P. gingivalis* Library for Sequencing.

To determine the DNA sequence of *P. gingivalis* genomic DNA was isolated from *P. gingivalis* strain W50 (ATCC 53978) essentially by the method described by Mamur J. ( J. Mol. Biol. 3, 208–218, 1961). Cloning of DNA fragments was performed essentially as described by Fleischmann et al., (Science; 269, 496–512, 1995). Briefly, purified genomic DNA from *P. gingivalis* was nebulized to fragment the DNA and was treated with Bal31 nuclease to create blunt ends then run twice through preparative 1% agarose gels. DNA fragments of 1.6–2.0 kb were excised from the gel and the DNA recovered. This DNA was then ligated to the vector pUC18 (Smal digested and dephosphorylated; Pharmacia) and electrophoresed through a 1% preparative agarose gel. The fragment comprising linear vector plus one insert was excised, purified and this process repeated to reduce any vector without insert contamination. The recovered vector plus insert DNA was blunt-ended with T4 DNA polymerase, then a final ligation to produce circular DNA was performed. Aliquots of *Epicurian Coli* Electroporation-Competent Cells (Stratagene) were transformed with the ligated DNA and plated out on SOB agar antibiotic diffusion plates containing X-gal and incubated at 37° C. overnight. Colonies with inserts appeared white and those without inserts (vector alone) appeared blue. Plates were stored at 4° C. until the white clones were picked and expanded for the extraction of plasmid DNA for sequencing.

DNA Sequencing

Plasmid DNA was prepared by picking bacterial colonies into 1.5 ml of LB, TB or SOB broth supplemented with 50–100 ug/ml Ampicillin in 96 deep well plates. Plasmid DNA was isolated using the QIAprep Spin or QIAprep 96 Turbo miniprep kits (QIAGEN GmbH, Germany). DNA was eluted into a 96 well gridded array and stored at −20° C.

Sequencing reactions were performed using ABI PRISM Dye Terminator and ABI PRISM BIGDye Terminator Cycle Sequencing Ready Reaction kits with AmpliTaq DNA polymerase FS (PE Applied Biosystems, Foster City, Calif.) using the M13 Universal forward and reverse sequencing primers. Sequence reactions were conducted on either a Perkin-Elmer GeneAmp 9700 (PE Applied Biosystems) or Hybaid PCR Express (Hybaid, UK) thermal cyclers. Sequencing reactions were analysed on ABI PRISM 377 DNA sequencers (PE Applied Biosystems).

Raw trace data files from the ABI 377 sequencer were manually trimmed using Staden Pregap (Laboratory of Molecular Biology, Medical Research Council, UK) running on a Sun Microsystems computer. Trimmed files were assembled into contigs using Staden Gap v4.1 and exported as a consensus file in FastA format for analysis. The sequences obtained are set out below in the Sequence Listings.

As mentioned above the polynucleotides of the invention may be used in recombinant production of P. gingivalis polypeptides. If desired the ORFs within the sequences set out in the Sequence Listings may be predicted. Prediction of open reading frames within the sequences may be made using well known programs such as GeneMark (Borodovsky M, Rudd K E, and E V Koonin. (1994). "Intrinsic and extrinsic approaches for detecting genes in a bacterial genome." Nucleic Acids Res. 22:4756–4767).

While methods for the production of recombinant polypeptides are well known to those skilled in the art an illustrative protocol which may be used is set out hereunder. Cloning, Expression and Purification of Recombinant P. gingivalis Genes.

Oligonucleotides to the 5' and 3' regions of the sequence of interest may be used to amplify the sequence of interest from a preparation of P. gingivalis genomic DNA using a thermostable DNA polymerase or similar nucleic acid amplification enzyme and a thermal cycler or similar device. The PCR fragment is purified, and digested with appropriate restriction enzymes and ligated into the corresponding sites of a plasmid which may then be transformed into a host, such as E. coli. A resulting clone containing the correct insert is selected and induced for the expression of the recombinant protein. Expression of the recombinant protein may be determined by SDS-PAGE analysis and Western Blot using antisera or an anti-hexahistidine antibody that detects the hexahistidine tag that may be fused to the P. gingivalis recombinant protein. The recombinant protein may be purified by disruption of the E. coli cells by sonication. In the cells lysates, the recombinant protein may be soluble in non-denaturing aqueous solutions, or be solubilised from inclusion bodies by detergents such as Triton X100, NOG and sarkosyl, or by denaturants such as urea or guanidine. Alternatively, proteins may be purified from cell fractions using detergents such as Triton X114. Thereafter, the solubilised protein preparation is diluted in binding buffer and bound to a Nickel-nitrilotriacetic acid column. After washing, bound proteins may be eluted with 1M imidazole in elution buffer. Following purification, samples may be dialysed against denaturing or non-denaturing solutions containing one or more of the detergents or denaturants mentioned above to remove the imidazole. The solution is concentrated as required and stored at 4° C. until used. Purity and antigenicity may be assessed by SDS-PAGE and Western Blot using selected antisera and the protein concentration determined by routine assay.

The recombinant polypeptides may be used to raise antibodies in a suitable animal. These antibodies and the polypeptides may used in routine assays, such as ELISA and RIA, to detect P. gingivalis infection. In addition the polypeptides can be used to raise an immune response in a subject to protect against, or reduce the severity of P. gingivalis infection. The polypeptides may also be used therapeutically as may be the antibodies.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6444799B1). An electronic copy of the "Sequence Listing" will also be available from the USPTO upon request and payment of the fee set forth in 37 CFR 1.19(b)(3).

What is claimed is:

1. An isolated polynucleotide of at least 30 nucleotides, the polynucleotide comprising a contiguous sequence of at least 30 nucleotides which is identical to a contiguous sequence of at least 30 nucleotides within a sequence selected from the group consisting of SEQ. ID. NOS: 176, 192, 214, 243, 273, 417, 524, 638, 758 and 1005 and sequences complementary thereto.

2. An isolated polynucleotide as claimed in claim 1 in which the polynucleotide is at least 50 nucleotides.

3. An isolated polynucleotide as claimed in claim 2 in which the polynucleotide is at least 100 nucleotides.

4. An isolated polynucleotide as claimed in claim 2 in which the polynucleotide comprises a contiguous sequence of at least 50 nucleotides which is identical to a contiguous sequence of at least 50 nucleotides within a sequence selected from the group consisting of SEQ. ID. NOS: 176, 192, 214, 243, 273, 417, 524, 638, 758 and 1005 and sequences complementary thereto.

5. An isolated polynucleotide as claimed in claim 3 in which the polynucleotide comprises a contiguous sequence of at least 100 nucleotides which is identical to a contiguous sequence of at least 100 nucleotides within a sequence selected from the group consisting of SEQ. ID. NOS: 176, 192, 214, 243, 273, 417, 524, 638, 758 and 1005 and sequences complementary thereto.

6. An isolated polynucleotide comprising at least 30 nucleotides, the polynucleotide having a sequence which hybridises under stringent conditions to a sequence selected from the group consisting of SEQ. ID. NOS: 176, 192, 214, 243, 273, 417, 524, 638, 758 and 1005 and sequences complementary thereto.

7. An isolated polynucleotide as claimed in claim 6 in which the polynucleotide is at least 50 nucleotides.

8. An isolated polynucleotide as claimed in claim 7 in which the polynucleotide is at least 100 nucleotides.

9. An isolated polynucleotide as claimed in claim 1 in which the polynucleotide further comprises a detectable label.

10. An isolated polynucleotide as claimed in claim 6 in which the polynucleotide further comprises a detectable label.

11. An isolated polynucleotide as claimed in claim 1 in which the polynucleotide is DNA.

12. A recombinant expression vector comprising the DNA as claimed in claim 1 operably linked to a transcription regulatory element.

13. A cell comprising the recombinant expression vector of claim 12.

14. An isolated polynucleotide as claimed in claim 6 in which the polynucleotide is DNA.

15. A recombinant expression vector comprising the DNA as claimed in claim 12 operably linked to a transcription regulatory element.

16. A cell comprising the recombinant expression vector as claimed in claim 13.

17. A method for producing a *P. gingivalis* polypeptide comprising culturing the cell as claimed in claim 16 under conditions that permit expression of the polypeptide and recovering the polypeptide.

* * * * *